(12) United States Patent
Kearney et al.

(10) Patent No.: US 7,390,408 B2
(45) Date of Patent: Jun. 24, 2008

(54) SHALLOW BED FLUID TREATMENT APPARATUS

(75) Inventors: Michael M. Kearney, Twin Falls, ID (US); Kenneth R. Peterson, Twin Falls, ID (US); Lawrence Valesquez, Twin Falls, ID (US)

(73) Assignee: Amalgamated Research, Inc., Twin Falls, ID (US)

( * ) Notice: Subject to any disclaimer, the term of this patent is extended or adjusted under 35 U.S.C. 154(b) by 0 days.

(21) Appl. No.: 10/867,968

(22) Filed: Jun. 14, 2004

(65) Prior Publication Data

US 2005/0000879 A1    Jan. 6, 2005

Related U.S. Application Data

(63) Continuation of application No. 09/769,881, filed on Jan. 25, 2001, now abandoned.

(60) Provisional application No. 60/178,397, filed on Jan. 27, 2000.

(51) Int. Cl.
*B01D 24/38* (2006.01)
(52) U.S. Cl. .................. 210/282; 210/289; 210/291
(58) Field of Classification Search ............ 210/266, 210/282, 284, 289, 291
See application file for complete search history.

(56) References Cited

U.S. PATENT DOCUMENTS

| | | | | |
|---|---|---|---|---|
| 3,849,306 A | | 11/1974 | Anderson | 210/685 |
| 3,925,202 A | * | 12/1975 | Hirs | 210/795 |
| 4,025,438 A | | 5/1977 | Gelman et al. | 210/484 |
| 4,059,528 A | | 11/1977 | Grosshandler | 210/282 |
| 4,648,976 A | * | 3/1987 | Chen | 210/678 |
| 4,673,507 A | | 6/1987 | Brown | 210/681 |
| 4,999,102 A | | 3/1991 | Cox et al. | 210/137 |
| 5,354,460 A | | 10/1994 | Kearney et al. | 210/198.2 |
| 5,626,750 A | | 5/1997 | Chinn | 210/275 |
| 5,938,333 A | | 8/1999 | Kearney | 366/336 |
| 6,333,019 B1 | | 12/2001 | Coppens | 423/659 |
| 6,616,327 B1 | | 9/2003 | Kearney et al. | 366/340 |

FOREIGN PATENT DOCUMENTS

| | | |
|---|---|---|
| DE | 41 18 501 A | 12/1992 |
| EP | 0 030 697 | 6/1981 |
| JP | 63 173960 A | 7/1988 |
| WO | WO98/14268 | 4/1998 |
| WO | WO99/48599 | 9/1999 |

* cited by examiner

*Primary Examiner*—Christopher Upton
(74) *Attorney, Agent, or Firm*—Trask Britt, P.C.

(57) ABSTRACT

A column apparatus containing a shallow bed of material between fluid transporting fractals of large active surface area results in highly efficient processing with small equipment size.

22 Claims, 7 Drawing Sheets

SHALLOW BED FLUID TREATMENT APPARATUS

CROSS-REFERENCE TO RELATED APPLICATION

This application is a continuation application of U.S. application Ser. No. 09/769,881, entitled "SHALLOW BED FLUID TREATMENT APPARATUS" filed on 25 Jan. 2001, now abandoned, which claims the benefit of the filing date of U.S. provisional patent application Ser. No. 60/178,397, filed 27 Jan. 2000 for "FLAT BED FLUID TREATMENT APPARATUS."

BACKGROUND OF THE INVENTION

1. Field of the Invention

Many fluid processes operate by passing fluids through beds of material. These processes include chromatography, ion exchange, adsorption, catalytic reaction, etc. This invention is directed to these processes in general.

2. State of the Art

Fluid processes characteristically exhibit severe limits on operation due to bed pressure drop, kinetics and flow uniformity. These limits are placed on, for example, productivity, process efficiency, energy use, system size, environmental compatibility, and capital/operating costs.

As one example of how these limits occur, the flow rate through a bed may be constrained because as flow rate increases, bed pressure drop increases. Pressure drop may reach a point where the pressure rating of a column containing the bed may be exceeded, the bed may begin to unacceptably compress, bed particles may be destroyed and excessive energy may be required for operation. Clearly, this effect places limits on productivity (limits on flow rate) and cell design and cost (higher pressure requires additional structural strength).

As another example, high linear velocities can result in unacceptably poor interaction or reaction of a fluid with the bed material. That is, the kinetic requirements of the system are self limiting. An excessively high linear velocity of a fluid through a bed will result in an insufficient contact time of the fluid with the bed particles. Clearly this places limits on productivity. (Again, flow rate is limited).

Spreading out a bed to a wide (large cross section), shallow (shallow depth or short travel path) geometry instead of a high (long travel path), narrow (relatively small cross section transverse to the direction of flow) geometry will reduce both the bed pressure drop and the linear velocity of a fluid passing through the bed. While both of these effects would be very beneficial, such column construction is not prevalent because of the difficulty of distributing and collecting fluid across a wide, shallow bed (a large cross section). Any inhomogeneity or turbulence in the fluid introduced into the column cannot normally be attenuated through a wide, shallow bed so the inhomogeneities are reflected as inefficiencies and unacceptable processing. For example, in chromatography, such problems result in band broadening and poor separation of the components of a feed mixture.

A representative device is disclosed in U.S. Pat. No. 4,673,507 to Brown. The '507 patent discloses a fluid treatment apparatus which can be used for shallow bed operation. However this device lacks significantly distributed fluid feed and collection systems and is dependent upon maintaining the bed in an over packed condition. A substantially uniform fluid flow distribution across the bed is achieved by employing resins of fine (substantially uniform) particle size which are maintained in an over packed condition. Here, the term 'over packed' is used to mean that the particles are confined within the resin bed so that they are subjected to compression at all times. This device inherently restricts process fluid flow across the bed.

U.S. Pat. No. 5,626,750 to Chinn discloses an apparatus for treating fluid. In this apparatus, first and second "particle free cavities" are provided above and below the retained particle bed. Even flow of fluid through the bed is provided simply by the pressure drop across the bed. The pressure drop across the bed is a function of the pressures in the first and second cavities. No provision is made to substantially control fluid flow characteristics (eddies, or turbulent zones) in process fluid streams near the bed surface.

It would be an advance to provide an apparatus for processing fluids which exhibits a reduced pressure drop through a bed of media, and also has a reduced fluid flow rate (velocity) at an increased volumetric flow rate through the bed. A preferred apparatus would provide control over process fluid flow to reduce mixing and turbulence near the bed to resist inhomogeneities in the processing stream.

BRIEF SUMMARY OF THE INVENTION

The present invention provides an apparatus for a fluid processing system which involves passing a fluid through a processing bed configured to have a diameter substantially greater than it's height (the distance between its inlet end and its outlet end). The invention is operable in systems in which the ratio of diameter (D) to height (h) of the processing bed is as high as 20:1 or more. The invention is advantageously applied to beds with D:h ratios approaching 2:1, but D:h ratios in excess of about 3:1 are presently preferred. The term "processing bed" refers to any confined mass of conventional or special purpose processing material (medium) contained by a cell or column through which fluids are passed. Typical such processing materials include inorganic or organic packing materials, chromatographic media, ion exchange media, absorption or adsorption media, enzymes and catalytic reactants.

A fluid distributor is typically arranged to introduce process fluid at the inlet end of the bed with a density of at least 200 distribution exits per square foot. A fluid collector is typically arranged to collect once processed fluid at the outlet end of the resin bed. It is generally preferred for the collector to be arranged to collect fluid through collection inlets with a density of at least 200 per square foot. It is within contemplation to provide inlets and/or exits with a density of 200 per square inch or more. It is currently preferred to construct the distributor and the collector from recursively arranged fractal elements. Systems according to the principles of the present invention may be constructed to produce processing flow conditions with a pressure drop across the media bed of less than 5 psi.

A system according to the present invention may further include a second processing bed with an inlet side, an outlet side, and a diameter at least twice the distance between the inlet side and the outlet side. A second fluid distributor may be arranged to introduce the once processed fluid to the inlet side of the second bed. The second distributor also desirably has a density of at least 200 distribution exits per square foot to promote one-dimensional flow with minimized mixing and turbulence in the process fluid. A second fluid collector is then generally arranged to collect twice processed fluid at the outlet side of the second resin bed. It is currently preferred for the first and second fluid distributors to be formed from fractal structure. It is also preferred that the first and second fluid collectors are formed from fractal structure, and are similar to the distributors. One desirable recursive fractal element may be characterized as having an "H" shape. Other fractal elements, including those with 3-dimensional shapes, are also within contemplation for use in either distributor or collector structures.

BRIEF DESCRIPTION OF THE SEVERAL VIEWS OF THE DRAWINGS

In the drawings, which illustrate what is currently regarded as the best mode for carrying out the invention and in which like reference numerals refer to like parts in different views or embodiments.

DETAILED DESCRIPTION OF THE INVENTION

Figure 1:
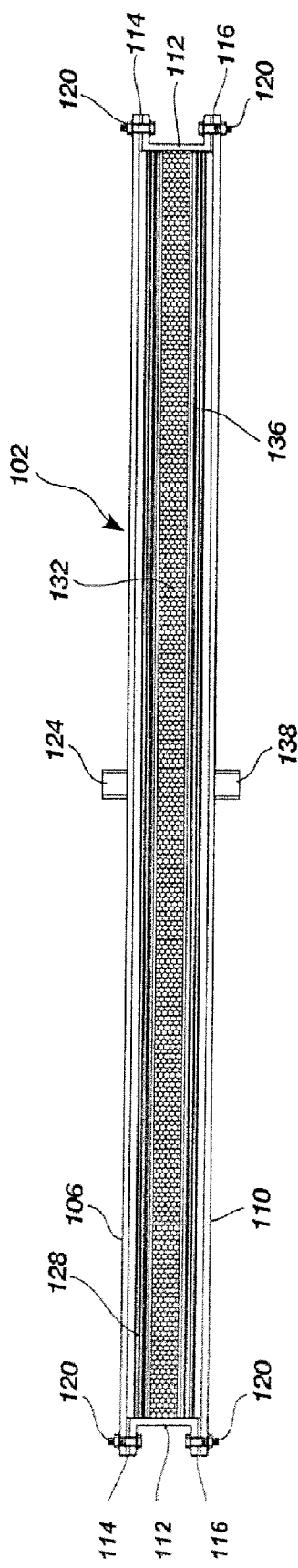
FIG. 1 is a plan view in cross-section of a typical embodiment of this invention.

FIG. 1 illustrates a typical fluid treatment apparatus according to this invention, generally indicated at 102. The apparatus typically includes a top plate 106, a bottom plate 110, and a side wall 112. As illustrated, side wall 112 forms a ring-like structure to enclose a volume between top and bottom plates 106 and 110. The apparatus will be described with reference to a substantially circular side wall 112, although such a structural limitation is not required for practice of this invention. One or more side walls 112 may be constructed to form virtually any shape in cross-section through the apparatus.

It is currently preferred to assemble top and bottom plates 106 and 110 to side wall 112 in fluid tight engagement with top and bottom gaskets 114 and 116 respectively. Joint structure which may be disassembled is generally preferred, such as the bolted joint interface indicated generally at 120, in the assembly of an apparatus 102.

With further reference to FIG. 1, top plate 106 generally carries one or more fluid ports 124 for passing process fluids there through. Fluid port 124 is desirably constructed in fluid communication with a distribution network of orifices arranged in a fractal distributor 128. A distributor 128 preferably functions to distribute the process fluid in a configuration approaching a homogeneous arrangement of inlet or exit points in space. The main purpose of such a distributor is to produce process fluid flow directed in substantially only one direction. It is currently preferred to provide distributor 128 as a fractal. A bed 132, formed of a suitable working media, is typically disposed between fractal distributors 128 and 136.

In operation under top-down flow, distributor 136 functions as a collector. A distributor 136 is typically similar in structure to the distributor 128, but in any case generally provides a homogeneous arrangement of inlet or exit points in space. Fluid port 138, in fluid communication with distributor 136, functions to pass process fluids through bottom plate 110. It may now be realized that process fluids introduced into apparatus 102 through port 124 may pass through bed 132 and be collected for exit through port 138. Process fluid may be distributed and collected in a substantially homogeneous fashion by fractal distributors 128 and 136 on opposite sides of the bed 132. The distributors 128 and 136 minimize turbulence and mixing in the process fluid in zones near the top and bottom surfaces of bed 132. Process fluid flow may alternatively be oppositely directed, with port 138 functioning as an inlet, and port 128 as an outlet port. For convenience, the apparatus will generally be described hereinafter with a top-down flow condition. In a top-down flow condition, top distributor 128 functions as a distributor, and bottom distributor 136 functions as a collector.

Figure 2:
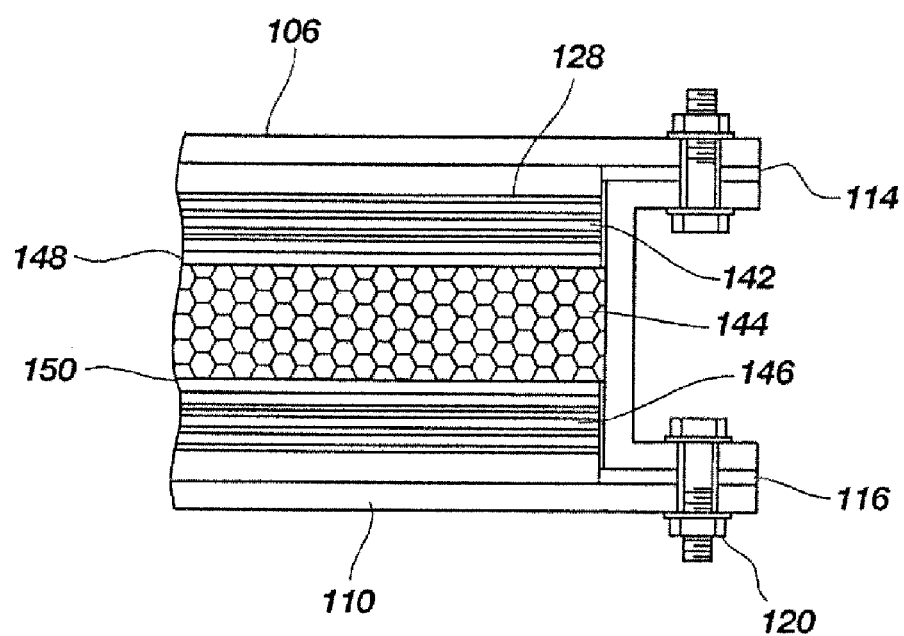
FIG. 2 is a close-up of an edge portion indicated by arrows 2-2 in FIG. 1.

FIG. 2 illustrates a close-up view of structure typically included in preferred embodiments of the invention. The illustration of FIG. 2 depicts typical mirror image construction on inlet and outlet sides of the device. Three zones are indicated through the height of the apparatus, representing a fractal distributor zone 142, a bed zone 144, and a second fractal distributor zone 146. Fractal distributor zone 142 houses fractal distributor 128, and fractal distributor zone 146 houses fractal distributor 136. The distributor zones do not have to fill the entire space between the bed 132 and the top or bottom plates 106 and 110 respectively. A space may be maintained, for example, above a bed 132 for purpose of fluidizing the bed 132.

The fractal distributor zones typically function to minimize mixing and turbulence near the bed surfaces. A distributor 128 or 136 desirably provides a population of fluid exits at a fluid/distributor interface to approximate a distributed fluid flow having only a component of velocity directed toward, or away from, a surface of the bed 132. Bed zone 144 houses bed 132 having top and bottom surfaces 148 and 150 respectively. Bed zone 144 may be defined by top and bottom surfaces formed by a screen, mesh, membrane, or other retaining elements (not illustrated).

Figure 3:
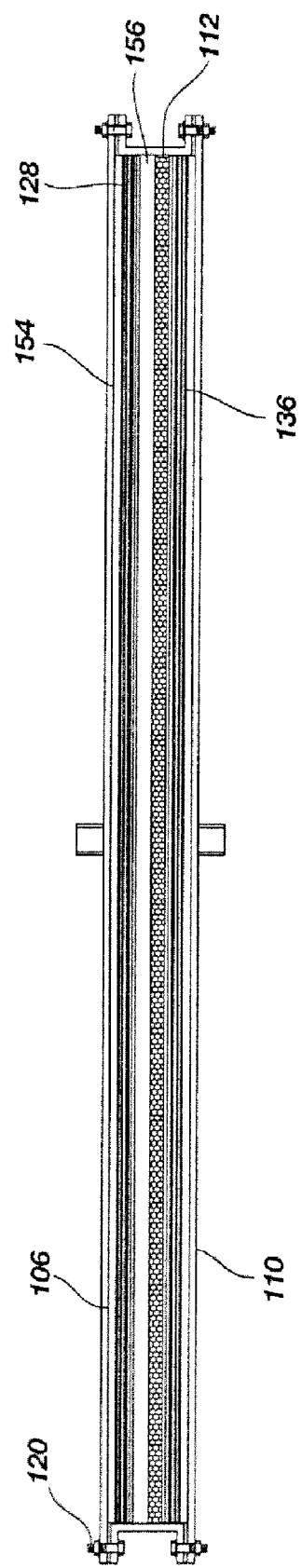
FIG. 3 is a plan view in cross-section of an alternate embodiment of this invention having a void space left between the bed and the top distributor.

FIG. 3 illustrates an alternative embodiment 154 of this invention with a void space 156 left between the bed 132 and the top distributor 128. The invention can operate efficiently in this configuration. This alternative embodiment 154 allows for internal fluidization which is necessary for common steps such as bed backwash or continuous fluidized bed operation. Void space 156 allows material of bed 132 sufficient space in which to move in a vertical direction for purpose of backwashing or to fluidize the bed 132.

Figure 4:
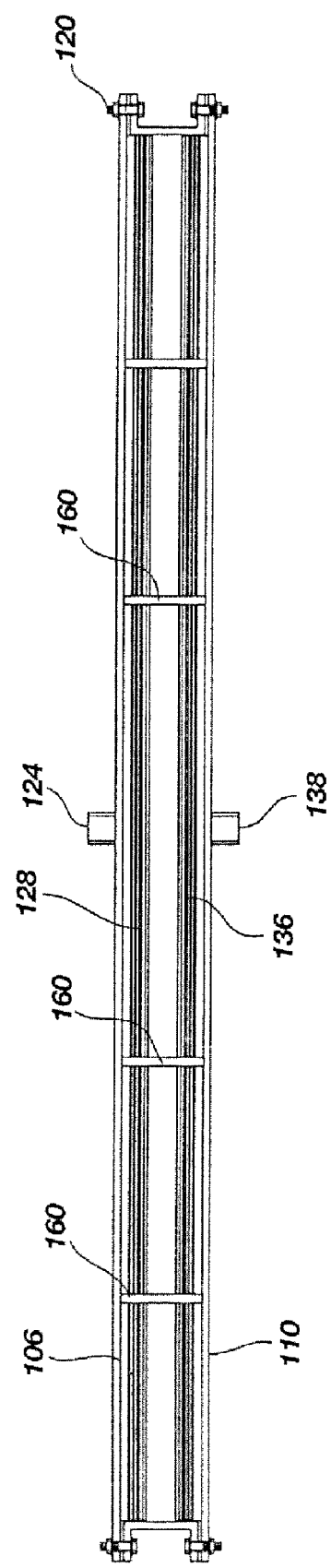
FIG. 4 is a plan view of an embodiment having supports for the end distributors.

FIG. 4 illustrates internal supports 160 which can be used if the diameter of the shallow cell becomes too large to properly support the end distributors. The supports 160 preferably intersect the fractal distributors 128 and 136 in blank areas to avoid any interference with process fluid flow. Rods or flat plate are examples of support structure which can be used in a support element 160.

Figure 5:
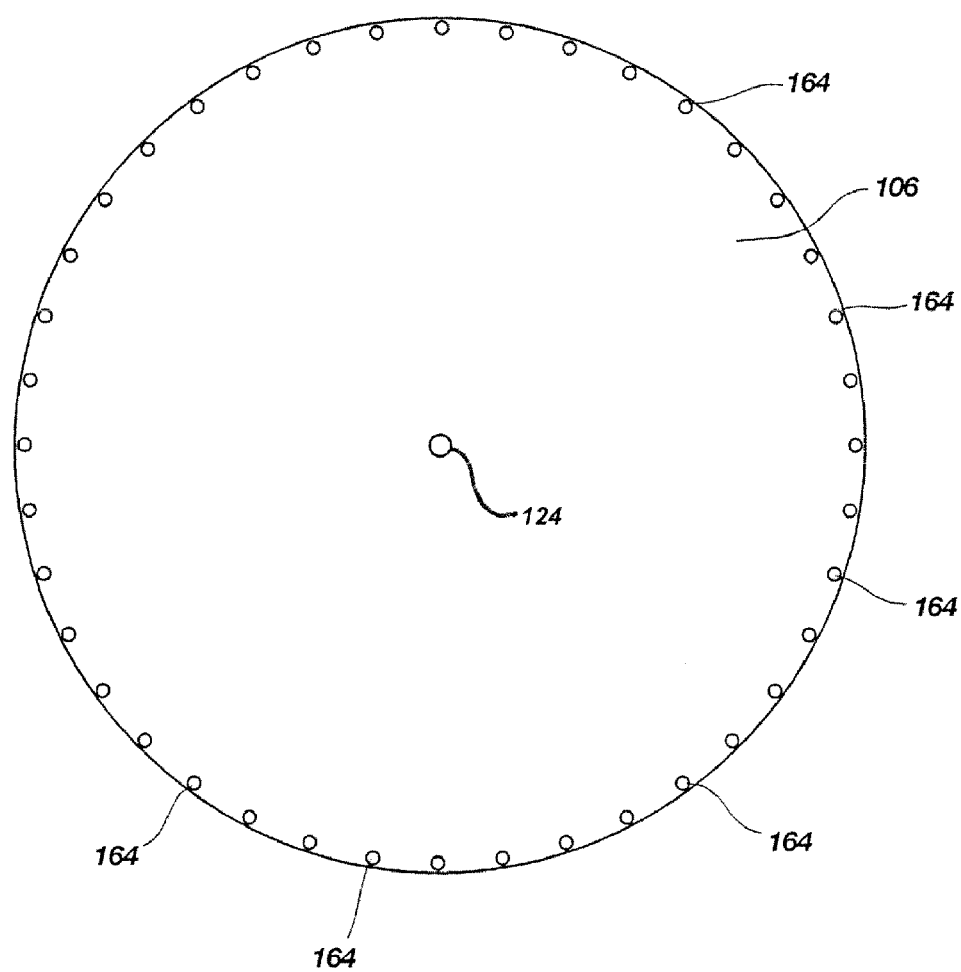
FIG. 5 is a top view of a typical top end plate.

FIG. 5 illustrates a top end plate 106 with a fluid port 124 located approximately on a central axis. One or more such ports 124 may be located at other, non axial locations. However, it is currently preferred to have only one such port 124 centrally located through end plate 106. The location of the port 124 may be determined by manufacturing concerns, and may thus be off centered. It is generally desired to provide port 124 at a location convenient for connection with distributor 128. A plurality of bolt holes 164 may be provided spaced around the perimeter of illustrated plate 106 to form joint structure 120. A bottom end plate 110 is typically structured similar to, or symmetric to, top plate 106.

Figure 6:
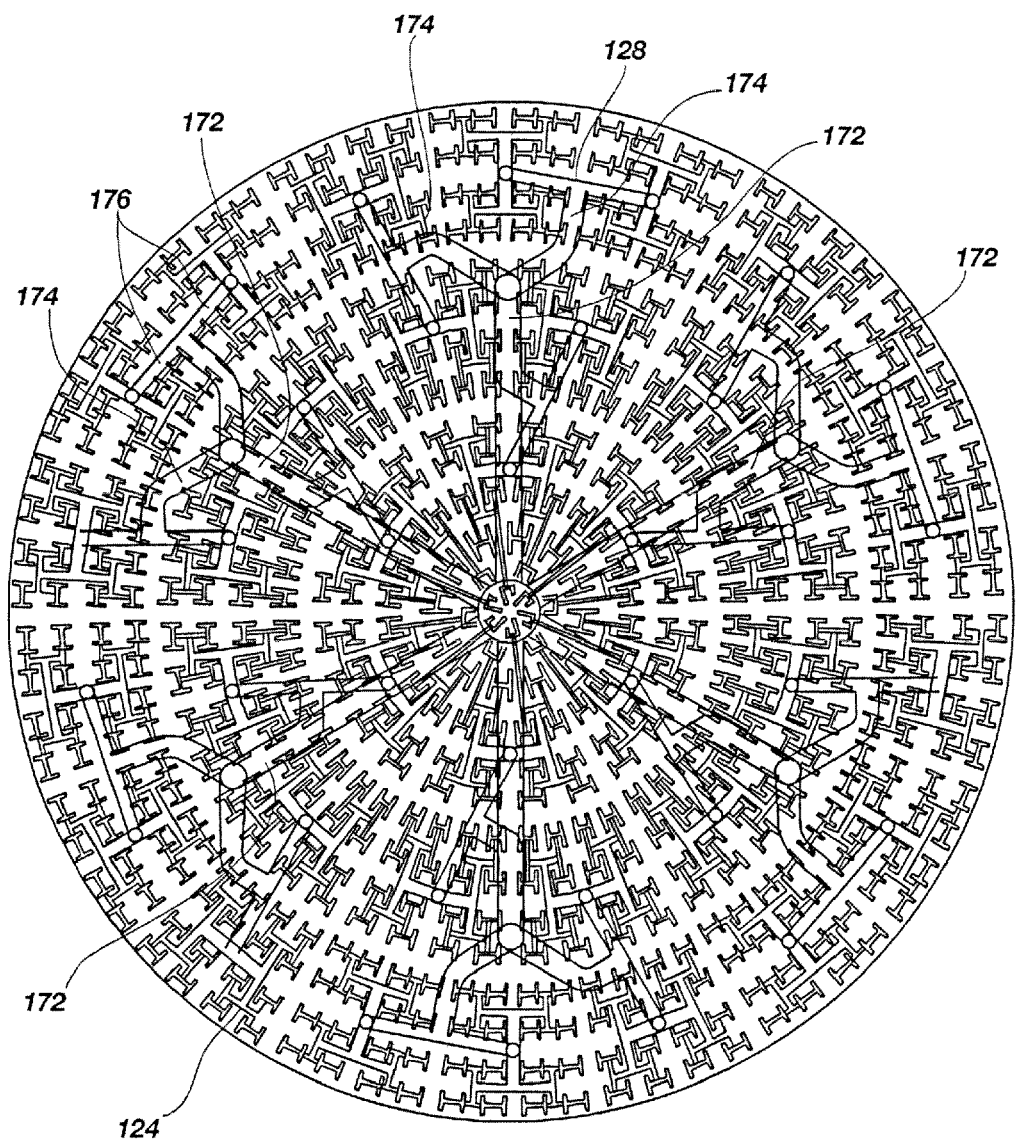
FIG. 6 is a top view of a representative fractal distributor embodiment.

FIG. 6 illustrates a typical fractal distributor embodiment 128 appropriate for this apparatus. The illustrated embodiment is only exemplary of a distributor 128, and represents only one desirable arrangement of distribution structure. A virtually infinite number of variations in structural configuration of a distributor 128 are workable.

Continuing to refer to FIG. 6, the individual conduits forming the distributor system 128 are placed on separate planes and do not intersect. Arcuate sectors 164 and 168 are illustrated in progressive stages of assembly. Fluid introduced to port 124 is divided to flow through successively divided conduit branches. As illustrated, fluid flowing from port 124 is divided into six conduits 172. Each of conduits 172 may subsequently be divided into three or six conduits 174 (can be mirror imaged in planes above and below conduits 172). Conduits 174 are then divided for fluid flow into multiple conduits 176. The recursive division process may be continued as desired to provide a sufficient density of fluid exits or entrances.

It is currently preferred to propagate successive divisions of the conduit structure in a recursive progression of fractal elements. Each successive division of conduits at least doubles the number of exits into the cell, and increasingly spreads the exits out into a distribution more uniform throughout the volume occupied by a distributor 128. Exits are not necessarily oriented to have an opening directed in the direction of overall flow from a distributor toward a bed. Simply spreading out the exits uniformly in a volume occupied by the distributor 128 promotes one-dimensional flow toward a bed 132, and minimizes turbulence in the process fluid.

The recursive addition of smaller and smaller conduits allows the apparatus to be built with progressively shallower cells and progressively shallower internal beds. As an example using fluid introduction to a cell, as the number of fluid exits increases, the distribution of such exit points becomes more homogeneous through a volume. The fluid introduced therefore has reduced turbulence or internal mixing. The resulting effect is for substantially the entire velocity vector describing the motion of the process fluid to be directed perpendicular to the bed. Ideally, a plane section through the introduced process fluid, and transverse to the direction of flow, would remain plane as the process fluid approaches and passes through the bed. As the fluid flow becomes more uniform, less attenuation of components of the fluid velocity vector is required from the bed itself, or from a boundary layer immediately adjacent the bed surface. Therefore the bed and processing cell may be correspondingly reduced in thickness, resulting in a "shallower" cell structure.

The term "fractal," as used in this disclosure, refers to a device constructed as a distributor or collector (128 or 136) having outlets or inlets connected through conduits constructed and arranged substantially in accordance with the principles of fractal geometry. Fractal structures are mathematical constructs which exhibit scale invariance. In such structures a self-similar geometry recurs at many scales. Typical distributors or collectors 128 or 136 are desirably configured of conduit arranged in fractal patterns using any well known fabrication technique, such as matrices of pipe, molded or machined tiles, or stamped plate. The outlet or inlet orifice density can be increased by recursively duplicating a basic pattern (fractal) on smaller and smaller scale.

A most simple fractal is a simple "T" intersection formed by intersecting a first conduit at a right angle with a second, generally smaller diameter, conduit. This simplest case doubles the number of inlets or outlets in a distribution system with each successive generation of fractal structure. Outlets of each generation of fractal structures are typically connected to inlets of the subsequent fractal generation. The outlets of the final generation of fractal structure correspond to the outlets of the distributor 128.

Figure 7:
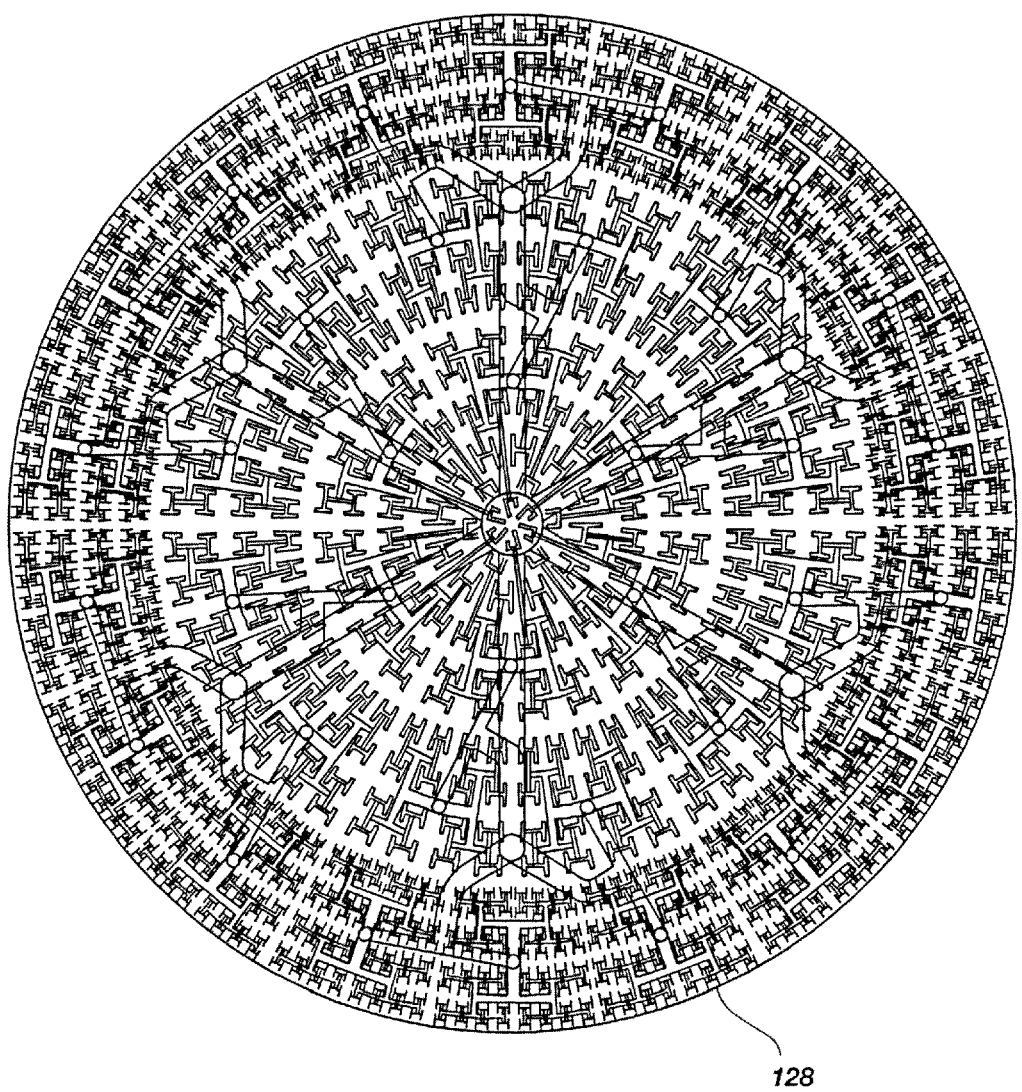
FIG. 7 is a top view of an alternative embodiment, similar to the fractal distributor of FIG. 6, but with an additional fractal iteration partially illustrated at the outside periphery.

Of course other, more complicated, fractal patterns are workable in the instant device. For example, a fractal pattern based upon recursively propagating a fractal element approximating an "H" shape is illustrated in FIGS. 6 and 7. Fractals may also be 3-dimensional. One 3-dimensional fractal element may be characterized as having four spokes radiating from a hub, with each spoke in fluid communication with paired exits. Such a fractal element may have exits located at the eight corners of an imaginary cube. A second 3-dimensional fractal element may have three spokes radiating from a hub. Each spoke may terminate in an exit, or communicate with additional conduit structure to form an increased number of exits. Furthermore, a distributor 128 or collector 136 may contain more than one fractal configuration. For example, one generation of "H" shaped fractal structures may feed a subsequent generation of "T" shaped fractal structures, and so on.

It is generally preferred that the total cross-section of successive generations of fractal structure is substantially the same as, or larger then, the total cross-section of the parent generation. Such a cross-section arrangement helps to minimize fluid velocity at the inlet and outlet orifices. In any case, it is desired that all conduit structures in a particular generation are hydraulically similar to promote evenly distributed flow throughout the generation.

FIG. 7 illustrates the same fractal propagation as in FIG. 6 but with an additional fractal iteration applied to the outside area. Such iterations are the key to this invention's progressive shrinkage of the height of the apparatus. FIG. 7 only shows the peripheral area additionally iterated for illustrative purposes. The iterative procedure of course applies to the entire volume of the fractal distributor zone to distribute exit or collection points throughout the volume occupied by a distributor 128 or 136. The number of additional iterations is only limited by manufacturing techniques.

The term "shallow," as used in this disclosure, is intended to distinguish over beds contained within a conventional column. According to this invention, a bed 132 of a given volume is configured with significantly reduced column height 144 (measured along the flow path of the traveling fluid, without regard to orientation) and a correspondingly increased cross sectional area (measured transverse the fluid flow path through the bed), as compared to a conventional bed configuration. Use of the shallow bed configuration enables the processing of a fluid through a bed 132 which is reduced in height by at least 70% compared to a given conventional fluid process. In fact, there is practically no limit on the reduction of bed height which can be achieved by the practice of this invention. In contrast to most conventional resin beds, those according to this invention are characterized by diameters significantly larger; typically at least double, their heights. Ratios of diameter to height in excess of 10:1 are practical, and ratios well in excess of 100:1 are also currently regarded as practical. As one example, the illustrated embodiment in FIG. 1 has a ratio of about 50:1.

While other cross sectional configurations are operable, a circular cross sectional bed configuration is currently preferred. The term "diameter," as applied to other than circular configurations, should be understood to mean "effective diameter;" that is, a dimension intermediate the major and minor axis of any such configuration.

While other worthwhile benefits result from the use of shallow cells in accordance with this invention, a particularly significant benefit is the reduction of certain process limiting characteristics. One useful benefit of this invention is the reduction of band broadening and fluid overlap. The present invention does not require over packed or compressed bed conditions. In fact, because the invention does not require over packed conditions, processes which require periodic or constant fluidization can be accomplished within the cell and still maintain the advantages of shallow bed operation. This reality greatly expands the possibilities for the use of the shallow bed concept. Neither does this invention require the particle free cavities of U.S. Pat. No. 5,626,750 and therefore will not exhibit the mixing effect which will occur in such chambers. Furthermore, one of the advances provided by this invention is avoiding processing limitations such as the pressure drop through the bed taught in the '750 patent.

Advantages of this Invention

1. Columns with very low bed depth or very high width to height ratio can be achieved.
2. An over packed bed is not required to obtain even flow distribution through the apparatus.
3. Substantial bed pressure drop is not required to obtain even flow distribution through the apparatus.
4. Flow rate to these devices can be increased significantly compared with conventional cell design because of a large decrease in pressure drop across the bed.
5. Flow rate to these apparatus can be increased significantly because of a large decrease in linear velocity through the bed compared to an equivalent volume of bed in a conventional high bed depth configuration.
6. Cost for equipment is reduced because the same flow rate to be treated can be passed through a much smaller and therefore less expensive column.
7. Because the equipment is smaller, there is a simple savings in space required for the equipment layout.
8. Building materials for equipment can be less robust and therefore less expensive because of the reduced structural requirements of this invention.
9. The invention creates possibilities for cell construction using a wide range of normally unacceptable materials.
10. Costs for bed materials are reduced since much less is needed for a given feed flow rate.
11. The reduced requirement for bed material allows ordinarily very expensive bed material to be used, therefore creating new opportunities previously denied due to bed material cost.
12. Because of the reduced pressure drop characteristics, highly compressible material can be used for bed packing and still maintain high productivity.
13. Because of reduced pressure drop characteristics, it is possible to use very small size bed particles and therefore obtain faster reaction rate (high surface area per unit volume).
14. When used for cycling equipment this invention allows such processes to cycle very rapidly. One result is that peripheral equipment can be much smaller than usual because equipment such as buffer tanks do not need to store as much material.
15. Energy required for process operation is reduced for a given bed material because of the reduction of bed pressure drop. For example, pumps to the process can be driven with less horsepower.
16. Fluid front overlap is reduced. Typical examples of such benefits which can be obtained with this invention include a reduction of the band broadening which occurs in chromatography and the reduction of fluid overlap in other applications.
17. The use of shallow cells provides the benefits listed above when used in single or multiple cell configurations. Examples of multiple cell configurations for which this invention is beneficial are primary/secondary/etc. series processing, simulated moving bed processes and carousel type fluid processing.

This invention enables the construction and operability of fluid processing with practically no limit on the "thinness" of the column bed. The advantages of very low bed pressure drop and reduced linear velocity through the bed are therefore realized. As earlier noted, there is practically no limit on the reduction of the column height because uniform fluid distribution can be recursively improved.

While less demanding applications may operate sufficiently with fractal density of at least 200 fluid exits (or collection points) per square foot at the fluid/distributor interface, for very fine distribution we recommend a density of at least 200 fluid exits (or collection points) per square inch Much higher densities are within contemplation, and it is recognized that progressively higher density will permit correspondingly progressively shallower bed geometry and higher efficiency of operation.

EXAMPLE 1

Pilot Test

This example describes a specific test, however this example is not meant to limit the scope of the invention. In fact, this particular application was chosen because it can clearly demonstrate in a single test many of the general benefits claimed above for shallow cell fluid processing with this invention. It should be clear that similar benefits will accrue for different fluid applications.

For this test, an ion exchange application was evaluated. Ion-exchange processes typically exhibit a large proportion of the problems and limits listed earlier. A shallow cell pilot system was designed to soften the "thin juice" from a sugar beet factory. Such material is typically softened in order to better suit it for downstream processes. In this ion exchange process, the hardness in the juice (calcium and magnesium) is exchanged for monovalent constituents, including $H^+$, and/or $Na^+$ and/or $K^+$.

A softening resin referred to as a weak cation exchange resin was used (Bayer CNP LF). The resin regenerant was sulfuric acid (hydrogen form regeneration) and the exhaustion material for softening was approximately 15% DS "thin juice" obtained in the processing of sugar beets. The feed material and regenerant are entirely conventional to weak cation thin juice softening.

A shallow cell was constructed with a diameter of 2 feet. Fractal distributors were used as mirror images for both the inlet distribution 128 and the outlet collection 132. Flow was allowed for both the downflow and upflow directions. The bed depth of the weak cation ion exchange resin was 6 inches. The bed D:h ratio was 4:1 To demonstrate that a shallow bed could be operated without the prior art requirement of an over packed bed, 6 inches of void space 156 above the bed 132 was included in the cell design (see FIG. 3).

Exhaustion was downflow at 500 bed volumes per hour. This means that a volume of juice was treated in an hour equal to 500 volumes of the bed of ion exchange resin. Operating temperature was 82° C. Regeneration was downflow with approximately 0.07 N $H_2SO_4$ at 150 bed volumes per hour.

Softening was entirely satisfactory with the shallow cell in comparison with a conventional industrial system. Composite softened product was typically from 0 to 0.02 grams CaO/

100 grams dry substance, which meets industry requirements for softened thin juice. Ordinarily, a shallow column of resin would be expected to leak hardness due to turbulence and poor kinetics, particularly if the flow rate/unit of resin is increased by a factor of 10. However, the shallow design of this invention allowed excellent results at 10 times the conventional feed flow rate. The reason is that the apparatus maintained a non turbulent and thoroughly homogeneous flow of fluid. Also, the low bed depth reduced the linear flow rate such that kinetics were still acceptable. If the same bed volume was configured in the conventional vertical manner and the flow rate increased as in this test, the linear velocity would have been too high for proper ion exchange kinetics. The fluid would have passed very quickly past the resin beads thus interfering with mass transfer. We also note that a conventional high bed at the high flow rates of this test would have resulted in extremely high pressure drop through the bed.

The following is a comparison of state of the art weak cation juice softening versus the shallow cell operation of this invention. The two systems were operated side by side in an industrial setting so the comparison includes having exactly comparable feed material.

| Conventional process equipment | | shallow bed test |
|---|---|---|
| Resin bed depth (inches) | 40 | 6 |
| Exhaustion flow rate BV/HR | 50 | 500 |
| Exhaustion pressure drop across the bed (psi) | 50-80 | 1.5 |
| Exhaustion cycle length (hours) | 12-24 | 3-4 |
| Sweeten-off BV/HR | 15 | 150 |
| Regeneration BV/HR | 30 | 150 |
| Regeneration rinse BV/HR | 15 | 150 |
| Backwash BV/HR | 30 | 200 |
| Feed hardness grams CaO/100 DS | .07 | .07 |
| Composite product hardness meq/100 DS | <.02 | <.02 |

Note that the shallow cell reduced the resin bed height required by 85%. This corresponds with our observation that the use of this invention generally reduces a given process bed depth by at least 70%.

A number of benefits were observed in this pilot test. First, the flow rate through the shallow cell was greater by 10× compared to conventional equipment. It is noted that the literature refers to very high resin productivity systems, in exactly this application, providing a maximum of 50 bed volumes/hour exhaustion flow rate. However, with the shallow cell apparatus, the feed flow is increased by an order of magnitude.

Because the productivity is increased by 10×, the amount of resin required is reduced by 10×. This means that the resin quantity is very small and the corresponding capital costs will be small. In this test, note the 85% reduction in resin requirement. The very small amount of resin also means that the equipment size is decreased by about 10× therefore resulting in less equipment cost and providing a valuable savings in equipment space requirements.

Because the pressure drop through the bed was reduced by about 95% to 98% it was possible to use a very low pressure vessel. This means that low expense thin wall construction can be used or the option is at hand to use low cost materials not ordinarily suitable for pressure vessels, e.g., low cost plastics. The low bed pressure drop also equates to less energy use required for fluid pumping.

The fast but efficient cycling of the test suggests that much smaller peripheral equipment can be used because buffer tanks for material such as regenerant and regenerant waste need only buffer 1/10 the conventional amount of material.

It is important to understand that if the bed volume in the pilot example is increased in size to allow for treatment of a larger amount of feed material, the very short bed depth will remain, or even be decreased. The additional bed volume is increased by increasing the width of the column. This is contrary to the usual scale-up methods which would rely on increasing the bed volume by adding height to the bed.

Note that this example also demonstrated that an over packed bed is not required for operation of this invention. This is indicated by the fact that upflow fluidization of the resin was possible (expansion by 100%) with no detrimental effects upon the subsequent regeneration or exhaustion steps.

Also note that this example demonstrated that bed pressure drop is not needed to cause the required even fluid distribution. In fact, bed pressure drop was reduced to only 1.5 psi compared with the conventional 50-80 psi. Therefore the instant apparatus operates at a bed pressure drop reduced by at least a factor of 30, compared to conventional devices. Even at a pressure drop of 5 psi across the bed, the instant device reduces processing pressure drop by at least an order of magnitude from that required by a conventional apparatus.

EXAMPLE 2

Flexibility of Construction for Progressively Fine Scaling

This invention can be applied over the entire range of fluid processing scales from very small scale applications to very large scale industrial use. The reason for this is that the fractal structures used in combination with shallow cell/shallow bed design provide a continuing scaling function as application scale changes.

Computer aided machining, molding and conduit construction techniques are appropriate for building the fractals. However, because this invention enables a nearly limitless and progressive reduction of processing bed depth, the practical problem may occur of how to manufacture progressively finer scaling structure.

To demonstrate the practical application of this invention, a fractal type as in FIG. 6 with very small feature size was constructed using stereolithography. The fractal was designed with final exit diameter of 0.015 inch. For this shallow cell application the fractal was designed as 10 plates. The plates were then manufactured as a monolithic part. Stereolithography is one technique which allows very fine feature size.

To further demonstrate that this invention is practically manufactured at the very small scales which provide for progressively wider and shallower functional bed depth, an identical fractal was manufactured using the technique of photochemical etching. This method introduces additional material options such as stainless steel and other metals.

It is noted that a particular manufacturing technique is not required to realize this invention, these examples only suggest the flexibility and immediate practicality of construction. Laser manufacturing techniques, micro-machining, nano-technology construction methods, ion deposition, etc. are appropriate and it is recognized that future manufacturing techniques for small scale structure will be likely suited for obtaining a desired shallowness of the apparatus.

Applicability of this Invention to Multi-Cell Processes

While the shallow cell apparatus of this invention can be used in single cell applications, a key purpose of this invention is to use such cells in multi-cell configurations. Shallowing multi-cell processes will result in the same benefits of high productivity, cost reductions etc.

Examples of multi-cell configurations which will benefit from the replacement of conventional cells with the shallow cells of this invention include:

1. Primary/secondary/etc. series type fluid processing. In such operations fluid flows out of a given cell and is then treated in a second and/or third etc.

2. Simulated moving bed technology. In this type process fluid passes through 2 or more beds or specified sections of stationary material. The movement of the bed is typically simulated using valve switching.

3. Carousel type systems. In this type of system columns are mounted on a turntable or a carousel and rotate around a central guide shaft and a central distribution valve.

Note that these suggestions of multi-cell use are not meant to limit the applicability of the invention. This invention is in general useful as a substitute for conventional bed depth fluid processes. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In a fluid processing system in which a fluid is caused to flow from a distributor, through a resin bed, to a collector, the improvement which comprises: providing said resin bed as a column having a diameter which is dimensionally larger than a height thereof; and
   providing said distributor as a fractal structure, said fractal structure including a plurality of individual conduits, said distributor being positioned elevationally above said resin bed, said distributor and said resin bed defining a void therebetween for facilitating bed backwash or continuous fluidized bed operation;
   providing said collector in a form of a second fractal structure, said second fractal structure including a plurality of individual conduits, said collector being positioned elevationally below said resin bed, said second fractal structure being placed in a mirror image position relative to said fractal structure of said distributor for collecting fluid exiting said resin bed.

2. An improvement according to claim 1, wherein the ratio of said diameter to said height is at least 2:1.

3. An improvement according to claim 1, wherein said distributor provides a population of fluid exits having a density greater than about 200 per square foot at a fluid/distributor interface.

4. An improvement according to claim 3, wherein said density is greater than about 200 per square inch.

5. An improvement according to claim 1, said system being configured and arranged to produce process fluid flow through said bed in response to a pressure drop across said bed of less than 5 psi.

6. An improvement according to claim 1, in combination with a second fluid processing system in which fluid is caused to flow from said collector to a second distributor, through a second bed of processing material, to a second collector, wherein said second distributor and second collector comprise fractal structure.

7. A fluid processing system comprising:
   a first resin bed with an inlet end, an outlet end, and a diameter at least twice the distance between said inlet end and said outlet end;
   a first fluid distributor constructed and arranged to introduce fluid at said inlet end of said resin bed at a density of at least 200 distribution exits per square foot, said distributor being positioned elevationally above said first resin bed, said distributor and said first resin bed defining a void therebetween for facilitating bed backwash or continuous fluidized bed operation; and
   a first fluid collector positioned elevationally below said first resin bed, said first fluid collector being placed in a mirror image relationship with said first fluid distributor, said first fluid collector being constructed and arranged to collect once processed fluid at said outlet end of said resin bed.

8. A system according to claim 7, wherein said collector is constructed and arranged to collect fluid through collection inlets at a density of at least 200 per square foot.

9. A system according to claim 8, wherein said distributor and said collector are fractals.

10. A system according to claim 8, wherein the ratio of diameter to height of said rosin bed is at least 10:1.

11. A system according to claim 7, wherein said system is constructed and arranged to produce processing flow conditions with a pressure drop across said bed of less than 5 psi.

12. A system according to claim 7, further comprising:
    a second resin bed with an inlet side, an outlet side, and a diameter at least twice the distance between said inlet side and said outlet side;
    a second fluid distributor constructed and arranged to introduce said once processed fluid at said inlet side of said second bed, said second distributor having a density of at least 200 distribution exits per square foot; and
    a second fluid collector constructed and arranged to collect twice processed fluid at said outlet side of said second resin bed.

13. A system according to claim 12, wherein said first and second fluid distributors comprise fractal structure.

14. A system according to claim 13, wherein said first and second fluid collectors comprise fractal structure.

15. A system according to claim 14, wherein a recursive fractal element may be characterized as having an "H" shape.

16. A fluid processing system comprising:
    a first resin bed with an inlet end, an outlet end, and a diameter at least twice the distance between said inlet end and said outlet end;
    a first fluid distributor, constructed and arranged to introduce fluid at said inlet end of said resin bed, said first fluid distributor including a plurality of conduits, each said conduit being divided into successive pluralities of conduit branches, said conduit branches being arranged in generations, each generation of conduit branches being positioned in a plane separate from conduits of a respective preceding and subsequent generation of conduit branches, said each said conduit branch having a distribution exit, said first fluid distributor having a density of at least 200 distribution exits per square foot; and
    a first fluid collector positioned elevationally below said first resin bed in a mirror image relationship with said first fluid distributor wherein each distribution exit of said distributor is positioned opposite a corresponding collection inlet of said first fluid collector, said first fluid collector being constructed and arranged to collect once processed fluid at said outlet end of said first resin bed, said distributor being positioned elevationally above said resin bed, said distributor and said resin bed defining a void therebetween for facilitating bed backwash or continuous fluidized bed operation.

17. In a fluid processing system in which a fluid is caused to flow from a distributor, through a resin bed, to a collector, the improvement which comprises:

providing said resin bed as a column having a diameter which is dimensionally larger than a height thereof; and providing said distributor as a fractal structure, said fractal structure including a plurality of individual conduits, said distributor being positioned elevationally above said resin bed; and providing said collector in a form of a second fractal structure, said second fractal structure including a plurality of individual conduits, said collector being positioned elevationally below said resin bed, said second fractal structure being placed in a mirror image position relative to said fractal structure of said distributor for collecting fluid exiting said resin bed.

18. An improvement according to claim 17, wherein the ratio of said diameter to said height is at least 2:1.

19. An improvement according to claim 17, wherein said distributor provides a population of fluid exits having a density greater than about 200 per square foot at a fluid/distributor interface.

20. An improvement according to claim 19, wherein said density is greater than about 200 per square inch.

21. An improvement according to claim 17, said system being configured and arranged to produce process fluid flow through said bed in response to a pressure drop across said bed of less than 5 psi.

22. An improvement according to claim 17, in combination with a second fluid processing system in which fluid is caused to flow from said collector to a second distributor, through a second bed of processing material, to a second collector, wherein said second distributor and second collector comprise fractal structure.

* * * * *